(12) United States Patent
Vanderlaan et al.

(10) Patent No.: US 8,158,695 B2
(45) Date of Patent: *Apr. 17, 2012

(54) FORMING CLEAR, WETTABLE SILICONE HYDROGEL ARTICLES WITHOUT SURFACE TREATMENTS

(75) Inventors: Douglas G. Vanderlaan, Jacksonville, FL (US); James R. Petisce, San Diego, CA (US); Azaam Alli, Jacksonville, FL (US); Kevin P. McCabe, St. Augustine Beach, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1471 days.

This patent is subject to a terminal disclaimer.

(21) Appl. No.: 10/794,399

(22) Filed: Mar. 5, 2004

(65) Prior Publication Data

US 2010/0280146 A1    Nov. 4, 2010

Related U.S. Application Data

(63) Continuation-in-part of application No. 10/236,538, filed on Sep. 6, 2002, now Pat. No. 6,822,016, and a continuation-in-part of application No. 10/236,762, filed on Sep. 6, 2002, now Pat. No. 7,052,131.

(60) Provisional application No. 60/452,898, filed on Mar. 7, 2003.

(51) Int. Cl.
*A61F 2/00* (2006.01)

(52) U.S. Cl. ......... 523/113; 523/114; 523/115; 523/116

(58) Field of Classification Search ........... 523/113–116
See application file for complete search history.

(56) References Cited

U.S. PATENT DOCUMENTS

| | | |
|---|---|---|
| 3,408,429 A | 10/1968 | Otto |
| 3,660,545 A | 5/1972 | Otto |
| 3,808,178 A | 4/1974 | Gaylord |
| 3,959,102 A | 5/1976 | Wajs |
| 4,113,224 A | 9/1978 | Clark |
| 4,120,570 A | 10/1978 | Gaylord |
| 4,136,250 A | 1/1979 | Mueller |
| 4,153,641 A | 5/1979 | Deichert |
| 4,190,277 A | 2/1980 | England |
| 4,197,266 A | 4/1980 | Clark |
| 4,260,725 A | 4/1981 | Keogh |
| 4,495,313 A | 1/1985 | Larsen |
| 4,680,336 A | 7/1987 | Larsen |
| 4,711,943 A | 12/1987 | Harvey, III |
| 4,740,533 A | 4/1988 | Su |
| 4,889,664 A | 12/1989 | Kindt-Larsen |
| 5,006,622 A | 4/1991 | Kunzler |
| 5,034,461 A | 7/1991 | Lai |
| 5,039,459 A | 8/1991 | Kindt Larsen |
| 5,062,995 A | 11/1991 | Wu |
| 5,070,215 A | 12/1991 | Bambury |
| 5,256,751 A | 10/1993 | Vanderlaan |
| 5,311,223 A | 5/1994 | Vanderlaan |
| 5,321,108 A | 6/1994 | Kunzler |
| 5,387,662 A | 2/1995 | Kunzler |
| 5,539,016 A | 7/1996 | Kunzler |
| 5,760,100 A | 6/1998 | Nicolson |
| 5,998,498 A | 12/1999 | Vanderlaan |
| 6,020,445 A | 2/2000 | Vanderlaan |
| 6,218,503 B1 | 4/2001 | Lai |
| 6,367,929 B1 * | 4/2002 | Maiden et al. ............ 351/160 H |
| 6,822,016 B2 * | 11/2004 | McCabe et al. ............... 523/107 |
| 7,052,131 B2 * | 5/2006 | McCabe et al. ........... 351/160 H |
| 2002/0107324 A1 | 8/2002 | Vanderlaan |
| 2003/0052424 A1 | 3/2003 | Turner et al. |
| 2003/0125498 A1 | 7/2003 | McCabe et al. |
| 2003/0162862 A1 | 8/2003 | McCabe et al. |
| 2004/0186248 A1 | 9/2004 | Vanderlaan |

FOREIGN PATENT DOCUMENTS

| | | |
|---|---|---|
| AU | 2004220102 B2 | 11/2008 |
| CN | 1218816 | 6/1999 |
| EP | 080539 | 6/1983 |
| EP | 0908744 | 4/1999 |
| EP | 1 386 924 | 2/2004 |
| EP | 940693 B1 | 6/2005 |
| JP | 11316358 A | 11/1999 |
| JP | 2003526449 A | 9/2003 |
| JP | 2005513173 A | 5/2005 |
| WO | WO 96/31792 | 10/1996 |
| WO | WO 01/70837 | 9/2001 |
| WO | WO 0170837 | 9/2001 |
| WO | WO 03011551 A1 | 2/2003 |
| WO | WO 03/022322 | 3/2003 |
| WO | WO 2004/081105 | 9/2004 |
| WO | WO 2004081105 | 9/2004 |

OTHER PUBLICATIONS

U.S. Appl. No. 60/452,898, filed Mar. 7, 2003, Johnson & Johnson Vision Care, Inc.
Encyclopedia of Polymer Science and Engineering, N-Vinyl Amide Polymers, Second edition, vol. 17, pp. 198-257, John Wiley & Sons Inc. Volume III, Photoinitiators for Free Radical Cationic & Anionic Photopolymerization, 2nd Edition by J.V. Crivello & K. Dietliker; edited by G. Bradley; John Wiley and Sons; New York; 1998.
Kamlet, M. J., Abboud, J. M., Abraham, M. H. and Taft, R. W.; J. Org. Chem., 1983, 48, 2877.
Barton, CRC Handbook of Solubility Par., 1st. Ed. 1983, p. 85-87 and using Tables 13, 14.

* cited by examiner

*Primary Examiner* — Edward J Cain
(74) *Attorney, Agent, or Firm* — Karen A. Harding

(57) ABSTRACT

The present invention is a composition, which may be used to form contact lenses, comprising at least one silicone containing component, at least one hydrophilic component, at least one high molecular weight hydrophilic polymer and at least one diluent with an alpha value of about 0.5 to about 1 and a Hansen solubility parameter of less than about 10.

41 Claims, 1 Drawing Sheet

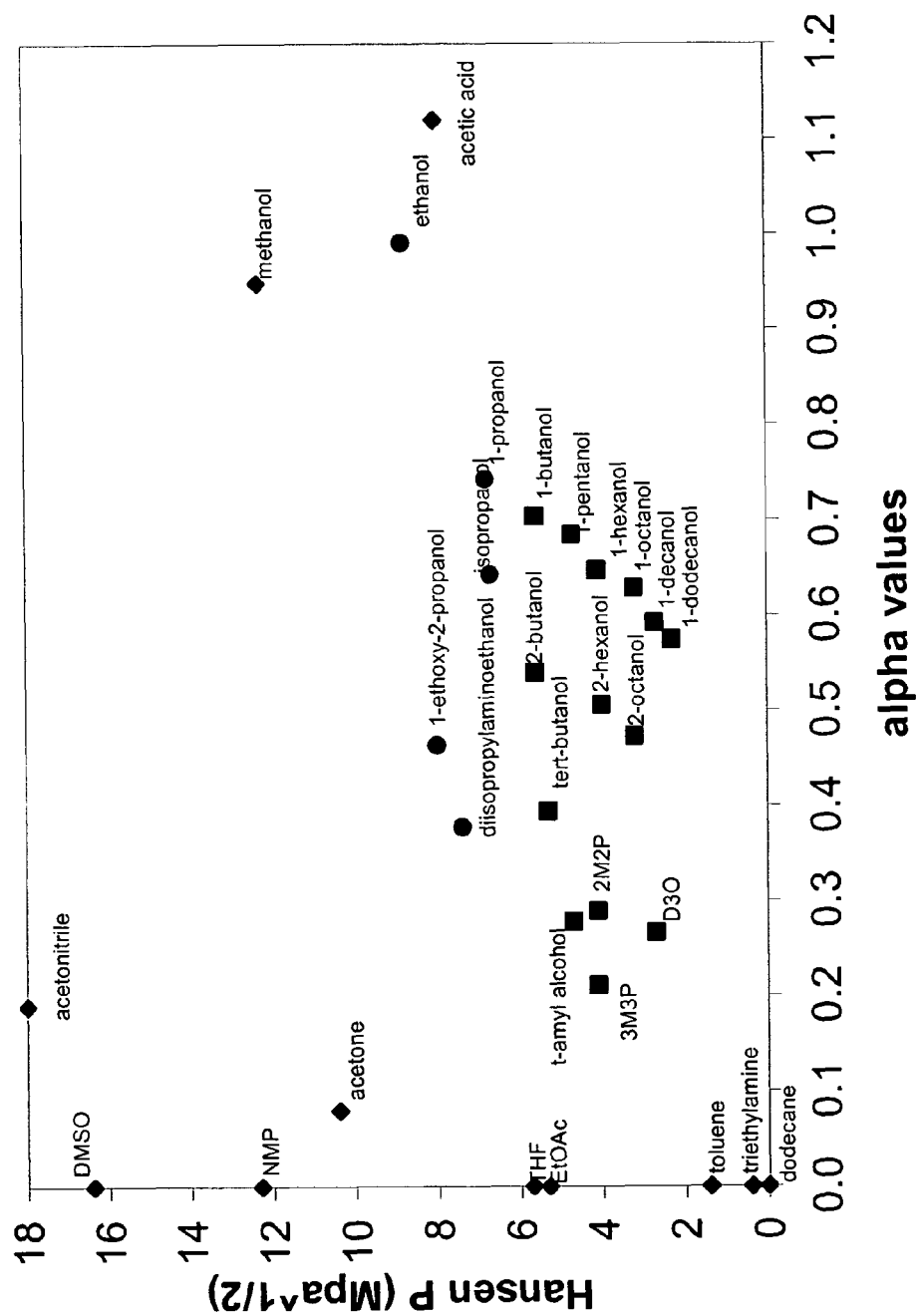

FORMING CLEAR, WETTABLE SILICONE HYDROGEL ARTICLES WITHOUT SURFACE TREATMENTS

CROSS REFERENCES TO RELATED APPLICATIONS

This application claims priority to provisional application Ser. No. 60/452,898, filed Mar. 7, 2003, and is a continuation-in-part of application Ser. No. 10/236,538, filed Sep. 6, 2002 now U.S. Pat. No. 6,822,016, and a continuation-in-part of application Ser. No. 10/236,762, filed Sep. 6, 2002 now U.S. Pat. No. 7,052,131, all of which are currently pending and are each hereby incorporated by reference.

FIELD OF THE INVENTION

The present invention relates to compatible compositions for forming molded articles and particularly medical devices such as contact lenses. More particularly, the present invention relates to a novel class of diluents, which allow the formation of compatible blends (and ultimately articles) comprising hydrophilic component(s), silicone containing component(s) and internal wetting agent(s).

BACKGROUND OF THE INVENTION

Silicone hydrogels have been prepared by polymerizing mixtures containing at least one silicone containing monomer and at least one hydrophilic monomer. Either the silicone containing monomer or the hydrophilic monomer may function as a crosslinking agent or a separate crosslinking agent may be employed. Various alcohols, including n-hexanol, ethanol, and n-nonanol have been used as diluents to compatibilize the silicone monomers and the hydrophilic monomers. However, the articles made from these components and diluents either did not form clear articles or were not sufficiently wettable to be used without a coating.

Primary and secondary alcohols having more than four carbon atoms have also been disclosed to be useful as diluents for silicone containing hydrogels. However, many of these diluents do not form clear, wettable articles when internal wetting agents are included in the reaction mixture. While these diluents are useful, many require an additional compatibilizing component to produce clear, wettable molded articles. Thus, there still remains a need in the art for silicone hydrogels which are polymerized in an economic and efficient way which may yield medical devices such as clear contact lenses. Silicone hydrogels comprise hydrophobic and hydrophilic compounds that have an inherent propensity to dissociate from each other. It is believed, without being limited to this mechanism, the observation of haze in lenses is likely attributable to the presence of phase separation on a scale that results in scattering of transmitted light. An imbalance in the polymerization rates or molar ratios of components may result in formation of blocks rich in one monomer, which may form haze.

Some commercially available silicone hydrogel lenses, such as Focus N&D (by Ciba Vision) and Purevision (by Bausch and Lomb) require specialized treatment in manufacture to impart surface wettability. The present invention produces silicone hydrogel lenses which contain internal wetting agents and do not need surface modification for surface wettability (lubricity) and clarity (lack of haze, as described below).

SUMMARY OF THE INVENTION

The present invention relates to compositions comprising at least one silicone containing component, at least one hydrophilic component, a high molecular weight hydrophilic polymer and at least one diluent having an alpha value of between about 0.05 and about 1 and a Hansen solubility parameter, δp of less than about 10, wherein the composition forms a clear solution (also referred to as a blend) at a selected reaction temperature, preferably up to about 75° C., more preferably about 35° to about 75° C., most preferably about 35° to about 65° C.

The present invention further relates to a composition comprising at least one silicone containing component, at least one hydroxyl containing component, at least one high molecular weight hydrophilic polymer and at least one diluent having an alpha value of between about 0.05 and about 1 and a Hansen solubility parameter, δp of less than about 10, optionally, a silicone containing compatibilizing component in an amount insufficient to compatibilize the blend in the absence of the diluent, wherein said composition forms a clear solution at a selected reaction temperature (also referred to as "compatibilizing").

The present invention further relates to a composition comprising at least one silicone containing component, at least one hydrophilic component, at least one high molecular weight hydrophilic polymer and at least one diluent which is capable at about ambient temperature of forming a compatible mixture. In a preferred embodiment, about 2 grams ("gm") of diluent is used in ratio of about 1.6 gm of said hydrophilic component, about 0.3 gm of said high molecular weight hydrophilic polymer, and about 1 gm silicone containing component.

Still further the present invention relates to methods for manufacturing devices, specifically ophthalmic devices and more specifically contact lenses and the articles so made. The present invention comprises contact lenses which may not be surface treated and are sufficiently wettable to be worn without substantial irritation to the eye.

BRIEF DESCRIPTION OF THE DRAWINGS

FIG. 1 is a graph depicting the Hansen solubility parameter, δp v. the alpha value for various diluents.

DETAILED DESCRIPTION OF THE SPECIFIC EMBODIMENTS

The present invention relates to compositions comprising at least one hydrophilic component, at least one silicone containing component, at least one high molecular weight hydrophilic polymer and at least one diluent, which is capable of compatibilizing the components without a compatibilizing agent.

As used herein, "diluent" refers to a diluent for the reactive composition. Diluents do not react to form part of the biomedical devices.

As used herein, "compatibilizing agent" means a compound containing at least one polymerizable group, which is capable of solubilizing the selected reactive components, but is used in an amount less than that which is required to solubilize the reactive components in the absence of a diluent. Preferable compatibilizing agents have a number average molecular weight of about less than 5000 Daltons, and more preferably less than about 3000 Daltons. The compatibilizing agent of the present invention solubilizes via hydrogen bonding, dispersive forces, combinations thereof and the like. Thus, any functionality which interacts in any of these ways with the high molecular weight hydrophilic polymer may be used as a compatibilizing agent. Compatibilizing agents in the present invention may be used in an amount insufficient to compatibilize the components of the composition absent a diluent. The amount will depend in part on the amount of high molecular weight hydrophilic polymer used.

As used herein, a "biomedical device" is any article that is designed to be used while either in or on mammalian tissues or fluid, and preferably in or on human tissue or fluids. Examples of these devices include but are not limited to catheters, implants, stents, and ophthalmic devices such as intraocular lenses and contact lenses. The preferred biomedical devices are ophthalmic devices, particularly contact lenses, most particularly contact lenses made from silicone hydrogels.

As used herein, the terms "lens" and "ophthalmic device" refer to devices that reside in or on the eye. These devices can provide optical correction, wound care, drug delivery, diagnostic functionality, cosmetic enhancement or effect or a combination of these properties. The term lens (or contact lens) includes but is not limited to soft contact lenses, hard contact lenses, intraocular lenses, overlay lenses, ocular inserts, and optical inserts.

All percentages in this specification are weight percentages unless otherwise noted.

As used herein, the phrase "without a surface treatment" or "not surface treated" means that the exterior surfaces of the devices of the present invention are not separately treated to improve the wettability of the device. Treatments which may be foregone because of the present invention include, plasma treatments, grafting, coating and the like. However, coatings which provide properties other than improved wettability, such as, but not limited to antimicrobial coatings and the application of color or other cosmetic enhancement, may be applied to devices of the present invention.

As used herein the term "silicone containing compatibilizing component" means reaction components which contain at least one silicone and at least one hydroxyl group. Such components have been disclosed in U.S. Ser. Nos. 10/236,538 and 10/236,762.

As used herein the term "precure form" means the composition has not yet been polymerized and cured to the final form of a biomedical device, preferably a contact lens.

Without being limited to this mechanism, it is believed that the nature of the diluent plays a critical role in delineating how the components copolymerize. Diluents may affect the solubility and aggregation characteristics of some monomers and may determine reactivity ratios. It is believed, without being limited to mechanism, that when one monomer cures significantly faster or slower than others and/or if a monomer is aggregated, hazy lenses are likely to form.

Suitable diluents include those, which possess both a hydrophilic and a hydrophobic nature. It has been found that the hydrophilic nature may be characterized by hydrogen donating ability, using Kamlet alpha values (also referred to as alpha values). The hydrophobic nature of the diluent may be characterized by the Hansen solubility parameter $\delta p$. Suitable diluents for the present invention are good hydrogen bond donors and polar. As used herein a "good" hydrogen bond donor, will donate hydrogen at least as readily as 3-methyl-3-pentanol. For certain diluents it is possible to measure the hydrogen bond donating ability by measuring the Kamlet alpha value (or as used herein "alpha value"). Suitable alpha values include those between about 0.05 and about 1 and preferably between about 0.1 and about 0.9.

The diluents useful in the present invention should also be relatively non-polar. The selected diluent should have a polarity sufficiently low to solubilize the non-polar components in the reactive mixture at reaction conditions. One way to characterize the polarity of the diluents of the present invention is via the Hansen solubility parameter, $\delta p$. In certain embodiments, the $\delta p$ is less than about 10, and preferably less than about 6. FIG. 1 depicts the Hansen p and alpha values for various diluents. Blends are the compositions used to form lenses before the compositions are cured, as would be understood by one of ordinary skill in the art.

It will be appreciated that the properties of the selected hydrophilic and hydrophobic components may effect the properties of the diluents which will provide the desired compatibilization. For example, if the reaction mixture contains only moderately polar components, diluents having moderate $\delta p$ may be used. If however, the reaction mixture contains strongly polar, components, the diluent may need to have a high $\delta p$.

Specific diluents which may be used include, without limitation, 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, SiGMA acetate, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino)ethanol mixtures thereof and the like.

Classes of suitable diluents include, without limitation, alcohols having 2 to 20 carbons, amides having 10 to 20 carbon atoms derived from primary amines and carboxylic acids having 8 to 20 carbon atoms. In some embodiments, primary and tertiary alcohols are preferred. Preferred classes include alcohols having 5 to 20 carbons and carboxylic acids having 10 to 20 carbon atoms.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like.

Mixtures of diluents may be used. In some embodiments it may be advantageous to use diluents with different properties. Moreover, it should be appreciated that when mixtures are used, the mixtures may include a diluent with properties within those specified herein and diluent(s) which do not possess the defined properties, or may contain diluents which each contain only one of the specified properties, so long as the alpha value and the $\delta p$ of the diluent mixture is within the values specified herein.

The diluents may be used in amounts up to about 50% by weight of the total of all components in the reactive mixture. More preferably the diluent is used in amounts less than about 45% and more preferably in amounts between about 15 and about 40% by weight of the total of all components in the reactive mixture.

In some embodiments, it is the diluent and the hydrophilic component which are required to generate both a clear blend and a clear biomedical device, such as a contact lens. In other embodiments, it is the diluent and the hydroxyl containing component which are required to generate both a clear blend and a clear biomedical device, such as a contact lens.

The one or more silicone containing components and one or more hydrophilic components used to make the polymer of this invention can be any of the known components used in the prior art to make silicone hydrogels. These terms silicone containing component and hydrophilic component are not mutually exclusive, in that, the silicone containing component can be somewhat hydrophilic and the hydrophilic component can comprise some because the silicone containing component can have hydrophilic groups and the hydrophilic components can have silicone groups.

Further, silicone containing component(s) and hydrophilic component(s) can be reacted prior to polymerization to form a prepolymer which is later polymerized in the presence of the diluent to form the polymer of this invention. When prepolymers or macromers are used, it is preferred to polymerize at least one silicone containing monomer and at least one hydrophilic monomer in the presence of the diluent, wherein the silicone containing monomers and the hydrophilic monomers differ. The term "monomer" used herein refers to low molecular weight compounds (i.e. typically having number average molecular weights less than 700) that can be polymerized. It is understood that the terms "silicone containing component" and "hydrophilic components" include "silicone containing monomers" and "hydrophilic monomers," respectively. Thus, it is understood that the terms "silicone containing monomers" and "hydrophilic monomers" include monomers, macromonomers and prepolymers.

A silicone containing component is one that contains at least one [—Si—O—Si] group, in a monomer, macromer or prepolymer. Preferably, the Si and attached O are present in the silicone containing component in an amount greater than 20 weight percent, and more preferably greater than 30 weight percent of the total molecular weight of the silicone containing component. Useful silicone containing components preferably comprise polymerizable functional groups such as acrylate, methacrylate, acrylamide, methacrylamide, N-vinyl lactam, N-vinylamide, and styryl functional groups. Examples of silicone containing components which are useful in this invention may be found in U.S. Pat. Nos. 3,808,178; 4,120,570; 4,136,250; 4,153,641; 4,740,533; 5,034,461 and 5,070,215, and EP080539. All of the patents cited herein are hereby incorporated in their entireties by reference. These references disclose many examples of olefinic silicone containing components.

Calculations

The following describes a calculation which may be useful in determining whether silicone hydrogel contact lenses with PVP will be hazy.

The moles of a component are calculated, as is known by one of ordinary skill in the art. Then the weight of silicon in a component is calculated by multiplying the grams of a component present in the composition by the weight fraction of the molecular weight that is comprised of silicon. For example, the molecular weight of SiMAA is 422.8 g. Since SiMAA contains three Si atoms, the weight fraction of Si is 3×28.09/422.8=0.199, where 28.09 g is the molecular weight of silicon. Therefore, the grams of silicon in X grams of SiMAA are 0.199*X. Then, the moles of silicon are calculated.

The grams of hydrogen bond donor groups ("HBD") in a component are calculated by multiplying the grams of a component in the formulation by the weight fraction HBD groups. For example, the molecular weight of HEMA is 130.14 g. Since HEMA contains one hydroxyl group, the weight fraction of HBD groups is 17/130.14=0.131. (Using 17 g for hydroxyl) Therefore, the grams of HBD groups in X grams of HEMA are 0.131*X.

The moles of HBD groups ('moles HBD') are calculated by dividing the grams of HBD groups present in a component by the molecular weight of the HBD group (17 g for hydroxyl (—OH), 15 g for amide (—NH)).

The grams of HBA (hydrogen bond acceptor) groups in a component ('grams HBA') are calculated by multiplying the grams of a component in the formulation by the weight fraction HBA groups. For example, the molecular weight of DMA is 99.13 g. Since DMA contains one HBA (amide carbonyl) group, the weight fraction of HBA groups is 28/99.13=0.282, where 28 g is the molecular weight of the amide carbonyl. The grams of HBA groups in X grams of DMA are 0.282*X. For PVP, the moles of HBA groups are calculated based on the molecular weight of the monomer repeating unit (111.14 g).

HTS ratio (HTS refers to hydrogen bond donor to silicon) is calculated by taking the sum of moles of HBD groups and dividing by the sum of the moles of silicon in the formulation, excluding diluent.

The moles HBD preferred are calculated by adding twice the number of moles of PVP present (including diluent) to the number of moles of HBA (hydrogen bond acceptor) groups from other sources. For the purposes of this specification, HBA groups are defined as carbonyls that are part of amide, carbamate, lactam, or urea functional groups.

The 'moles HBD to moles HBA (HMWHP) ratio' is calculated by dividing the number of moles of HBD groups present in the formulation (excluding diluent) by the number of moles of HBA groups present in the high molecular weight hydrophilic polymer (referred to as "HMWHP") (e.g. PVP).

The 'Ratio of moles HBD present to moles HBD preferred' is calculated by dividing the total number of moles of HBD groups in the formulation (including diluent) by the calculated number of moles of HBD groups needed.

In lenses formed from compositions containing PVP, the following are the preferred ratios. The preferred range of 'moles HBD to moles HBA (HMWHP) ratio' is $\geq$ about 0.8, more preferred is $\geq$ about 0.8 to $\leq$ about 5, more preferred is $\geq$ about 1.3 to $\leq$ about 5, and most preferred is $\geq$ about 1.7 to $\leq$ about 5. The preferred range for 'Ratio of moles HBD present to moles HBD preferred' is $\geq$ about 0.6, more preferred is $\geq$ about 0.6 to < about 4.5, more preferred is $\geq$ about 0.8 to < about 4.5, and most preferred is $\geq$ about 1.0 to $\leq$ about 3.0. The preferred range for 'HTS ratio' is > about 0.14, more preferred is > about 0.17 to $\leq$ about 0.35, and most preferred is > about 0.18 to $\leq$ about 0.35. One of ordinary skill in the art would understand that these calculations are useful for other contact lenses of the present invention but may have different preferred ranges depending on the HMWHP used.

EXAMPLES

Further examples of suitable silicone containing monomers are polysiloxanylalkyl(meth)acrylic monomers represented by the following formula:

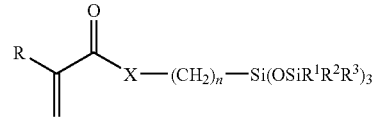

Formula I wherein: R denotes H or lower alkyl; X denotes O or $NR^4$; each $R^4$ independently denotes hydrogen or methyl, each $R^1$-$R^3$ independently denotes a lower alkyl radical or a phenyl radical, and n is 1 or 3 to 10.

Examples of these polysiloxanylalkyl (meth)acrylic monomers include methacryloxypropyl tris(trimethylsiloxy) silane, pentamethyldisiloxanyl methylmethacrylate, and methyldi(trimethylsiloxy)methacryloxymethyl silane. Methacryloxypropyl tris(trimethylsiloxy)silane is the most preferred.

One preferred class of silicone containing components is a poly(organosiloxane) prepolymer represented by formula II:

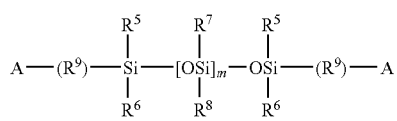

Formula II wherein each A independently denotes an activated unsaturated group, such as an ester or amide of an acrylic or a methacrylic acid or an alkyl or aryl group (providing that at least one A comprises an activated unsaturated group capable of undergoing radical polymerization); each of $R^5$, $R^6$, $R^7$ and $R^8$ are independently selected from the group consisting of a monovalent hydrocarbon radical or a halogen substituted monovalent hydrocarbon radical having 1 to 18 carbon atoms which may have ether linkages between carbon atoms;

$R^9$ denotes a divalent hydrocarbon radical having from 1 to 22 carbon atoms, and m is 0 or an integer greater than or equal to 1, and preferable 5 to 400, and more preferably 10 to 300. One specific example is α,ω-bismethacryloxypropyl poly-dimethyl-siloxane. Another preferred example is mPDMS (monomethacryloxypropyl terminated mono-n-butyl terminated polydimethylsiloxane).

Another useful class of silicone containing components includes silicone containing vinyl carbonate or vinyl carbamate monomers of the following formula:

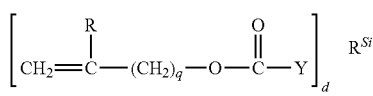

Formula III wherein: Y denotes O, S. or NH; $R^{si}$ denotes a silicone containing organic radical; R denotes hydrogen or methyl; d is 1, 2, 3 or 4; and q is 0 or 1. Suitable silicone containing organic radicals $R^{Si}$ include the following:

 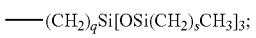

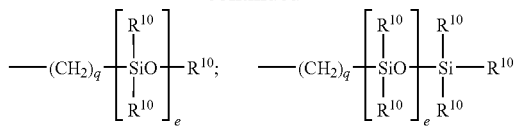

wherein $R^{10}$ denotes:

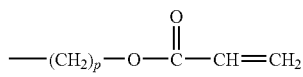

Wherein p is 1 to 6; or an alkyl radical or a fluoroalkyl radical having 1 to 6 carbon atoms; e is 1 to 200; q is 1, 2, 3 or 4; and s is 0, 1, 2, 3, 4 or 5.

The silicone containing vinyl carbonate or vinyl carbamate monomers specifically include: 1,3-bis[4-(vinyloxycarbonyloxy)but-1-yl]tetramethyl-siloxane 3-(vinyloxycarbonylthio) propyl-[tris(trimethylsiloxysilane]; 3-[tris(trimethylsiloxy)silyl]propyl allyl carbamate; 3-[tris(trimethylsiloxy) silyl]propyl vinyl carbamate; trimethylsilylethyl vinyl carbonate; trimethylsilylmethyl vinyl carbonate, and

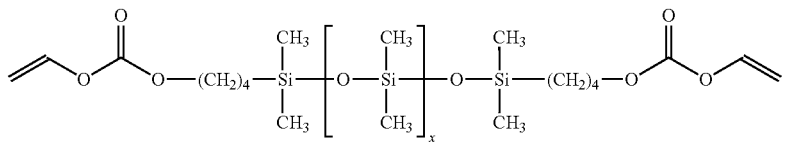

wherein x=25

Another class of silicone containing components includes compounds of the following formulae:

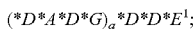

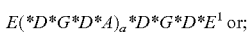

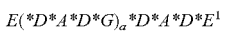

Formulae IV-VI wherein:
D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$a$ is at least 1;

A denotes a divalent polymeric radical of formula:

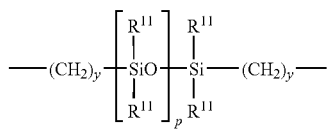

Formula VII $R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

Formula VIII

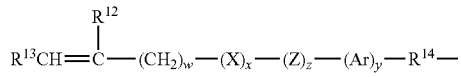

wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; v is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone containing component is represented by the following formula:

Formula IX

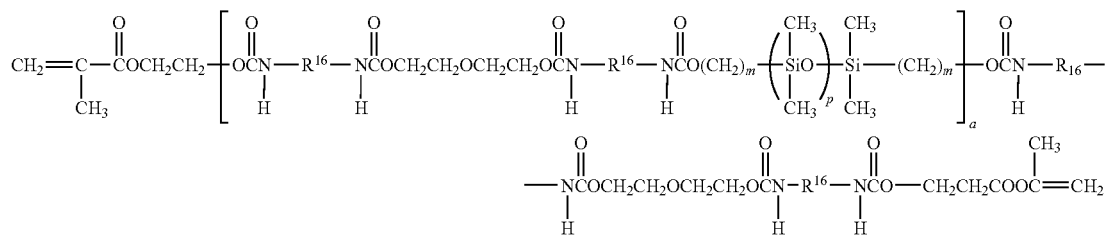

wherein $R^{16}$ is a diradical of a diisocyanate after removal of the isocyanate group, such as the diradical of isophorone diisocyanate. Another preferred silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

ether and polysaccharide groups. U.S. Pat. Nos. 5,321,108; 5,387,662 and 5,539,016 describe polysiloxanes with a polar fluorinated graft or side group having a hydrogen atom attached to a terminal difluoro-substituted carbon atom. Such polysiloxanes can also be used as the silicone monomer in this invention.

Hydrophilic components include those which are capable of providing at least about 20% and preferably at least about 25% water content to the resulting lens when combined with the remaining reactive components. Suitable hydrophilic components may be present in amounts between about 10 to about 60 weight % based upon the weight of all reactive components, preferably about 15 to about 50 weight %, and more preferably between about 20 to about 40 weight %. The hydrophilic monomers that may be used to make the polymers of this invention have at least one polymerizable double bond and at least one hydrophilic functional group. Examples of polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. Such hydrophilic monomers may themselves be used as crosslinking agents. "Acrylic-type" or "acrylic-containing" monomers are those monomers containing the acrylic group (CR'H═CRCOX) wherein R is H or $CH_3$, R' is H, alkyl or carbonyl, and X is O or N, which are also known to polymerize readily, such as Formula X

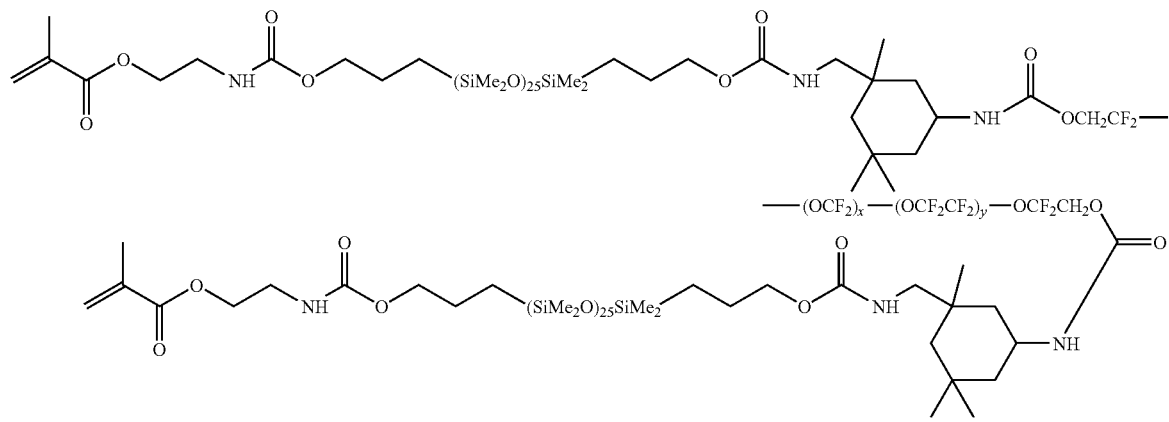

Other silicone containing components suitable for use in this invention include those described in WO 96/31792 such as macromers containing polysiloxane, polyalkylene ether, diisocyanate, polyfluorinated hydrocarbon, polyfluorinated N,N-dimethylacrylamide (DMA), 2-hydroxyethyl acrylate, glycerol methacrylate, 2-hydroxyethyl methacrylamide, polyethyleneglycol monomethacrylate, methacrylic acid, acrylic acid and mixtures thereof.

Hydrophilic vinyl-containing monomers which may be incorporated into the hydrogels of the present invention include monomers such as N-vinyl lactams (e.g. N-vinyl pyrrolidone (NVP)), N-vinyl-N-methyl acetamide, N-vinyl-N-ethyl acetamide, N-vinyl-N-ethyl formamide, N-vinyl formamide, N-2-hydroxyethyl vinyl carbamate, N-carboxy-β-alanine N-vinyl ester, with NVP being preferred.

Other hydrophilic monomers that can be employed in the invention include polyoxyethylene polyols having one or more of the terminal hydroxyl groups replaced with a functional group containing a polymerizable double bond. Examples include polyethylene glycol with one or more of the terminal hydroxyl groups replaced with a functional group containing a polymerizable double bond. Examples include polyethylene glycol reacted with one or more molar equivalents of an end-capping group such as isocyanatoethyl methacrylate ("IEM"), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,190,277. Other suitable hydrophilic monomers will be apparent to one skilled in the art.

More preferred hydrophilic monomers which may be incorporated into the polymer of the present invention include hydrophilic monomers such as N,N-dimethyl acrylamide (DMA), 2-hydroxyethyl acrylate, glycerol methacrylate, 2-hydroxyethyl methacrylamide, N-vinylpyrrolidone (NVP), HEMA, and polyethyleneglycol monomethacrylate.

Most preferred hydrophilic monomers include DMA, NVP, HEMA and mixtures thereof.

As used herein, "high molecular weight hydrophilic polymer" refers to substances having a weight average molecular weight of no less than about 100,000 Daltons, wherein said substances upon incorporation to silicone hydrogel formulations, increase the wettability of the cured silicone hydrogels. The preferred weight average molecular weight of these high molecular weight hydrophilic polymers is greater than about 150,000; more preferably between about 150,000 to about 2,000,000 Daltons, more preferably still between about 300,000 to about 1,800,000 Daltons, most preferably about 500,000 to about 1,500,000 Daltons.

Alternatively, the molecular weight of hydrophilic polymers of the invention can be also expressed by the K-value, based on kinematic viscosity measurements, as described in Encyclopedia of Polymer Science and Engineering, N-Vinyl Amide Polymers, Second edition, Vol 17, pgs. 198-257, John Wiley & Sons Inc. When expressed in this manner, hydrophilic monomers having K-values of greater than about 46 and preferably between about 46 and about 150. The high molecular weight hydrophilic polymers are present in the formulations of these devices in an amount sufficient to provide contact lenses and provide at least a 10% improvement in wettability and preferably provide wettable lenses (even without surface treatments). For a contact lens, "wettable" is a lens which displays an advancing dynamic contact angle of less than about 80°, preferably less than 70° and more preferably less than about 60°.

Suitable amounts of high molecular weight hydrophilic polymer include from about 1 to about 15 weight percent, more preferably about 3 to about 15 percent, most preferably about 3 to about 12 percent, all based upon the total of all reactive components.

Examples of high molecular weight hydrophilic polymers include but are not limited to polyamides, polylactones, polyimides, polylactams and functionalized polyamides, polylactones, polyimides, polylactams, such as DMA functionalized by copolymerizing DMA with a lesser molar amount of a hydroxyl-functional monomer such as HEMA, and then reacting the hydroxyl groups of the resulting copolymer with materials containing radical polymerizable groups, such as isocyanatoethylmethacrylate or methacryloyl chloride. Hydrophilic prepolymers made from DMA or n-vinyl pyrrolidone with glycidyl methacrylate may also be used. The glycidyl methacrylate ring can be opened to give a diol which may be used in conjunction with other hydrophilic prepolymer in a mixed system to increase the compatibility of the high molecular weight hydrophilic polymer, hydroxyl-functionalized silicone containing monomer and any other groups which impart compatibility. The preferred high molecular weight hydrophilic polymers are those that contain a cyclic moiety in their backbone, more preferably, a cyclic amide or cyclic imide. High molecular weight hydrophilic polymers include but are not limited to poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N—N-dimethylacrylamide, polyvinyl alcohol, polyacrylic acid, polyethylene-oxide, poly-2-ethyl-oxazoline, heparin polysaccharides, polysaccharides, mixtures and copolymers (including block or random, branched, multichain, comb-shaped or star shaped) thereof, where poly-N-vinylpyrrolidone (PVP) is particularly preferred. Copolymers might also be used such as graft copolymers of PVP.

In certain embodiments, it is preferred to have at least 3 weight % HEMA, more preferred to have at least 5 weight % HEMA, and most preferred to have at least 6 weight % HEMA.

The high molecular weight hydrophilic polymers provide improved wettability, and particularly improved in vivo wettability to the medical devices of the present invention. Without being bound by any theory, it is believed that the high molecular weight hydrophilic polymers are hydrogen bond receivers which in aqueous environments, hydrogen bond to water, thus becoming effectively more hydrophilic. The absence of water facilitates the incorporation of the hydrophilic polymer in the reaction mixture. Aside from the specifically named high molecular weight hydrophilic polymers, it is expected that any high molecular weight polymer will be useful in this invention provided that when said polymer is added to a silicone hydrogel formulation, the hydrophilic polymer (a) does not substantially phase separate from the reaction mixture and (b) imparts wettability to the resulting cured polymer. In some embodiments it is preferred that the high molecular weight hydrophilic polymer be soluble in the diluent at reaction temperatures. Manufacturing processes which use water or water soluble diluents may be preferred due to their simplicity and reduced cost. In these embodiments high molecular weight hydrophilic polymers which are water soluble at processing temperatures are preferred.

In certain embodiments a hydroxyl containing component is also included. The hydroxyl containing component that may be used to make the polymers of this invention have at least one polymerizable double bond and at least one hydrophilic functional group. Examples of polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. The hydroxyl containing component may also act as a crosslinking agent. In addition the hydroxyl containing component comprises a hydroxyl group. This hydroxyl group may be a primary, secondary or tertiary alcohol group, and may be located on an alkyl or aryl group. Examples of hydroxyl containing monomers that may be used include but are not limited to 2-hydroxyethyl methacrylate ("HEMA"), 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate, hydroxyoctyl methacrylate and other hydroxyl functional monomers as disclosed in U.S. Pat. Nos. 5,006,622; 5,070,215; 5,256,751 and 5,311,223. Preferred hydrophilic components include 2-hydroxyethyl methacrylate.

It is generally necessary to add one or more cross-linking agents, also referred to as cross-linking monomers, to the reaction mixture, such as ethylene glycol dimethacrylate ("EGDMA"), trimethylolpropane trimethacrylate ("TMPTMA"), glycerol trimethacrylate, polyethylene glycol dimethacrylate (wherein the polyethylene glycol preferably has a molecular weight up to, e.g., about 5000), and other polyacrylate and polymethacrylate esters, such as the end-capped polyoxyethylene polyols described above containing two or more terminal methacrylate moieties. The cross-linking agents are used in the usual amounts, e.g., from about 0.000415 to about 0.0156 mole per 100 grams of reactive components in the reaction mixture. (The reactive components are everything in the reaction mixture except the diluent and any additional processing aids which do not become part of the structure of the polymer.) Alternatively, if the hydrophilic monomers and/or the silicone containing monomers act as the cross-linking agent, the addition of a crosslinking agent to the reaction mixture is optional. Examples of hydrophilic monomers which can act as the crosslinking agent and when present do not require the addition of an additional crosslinking agent to the reaction mixture include polyoxyethylene polyols described above containing two or more terminal methacrylate moieties.

An example of a silicone containing monomer which can act as a crosslinking agent and, when present, does not require the addition of a crosslinking monomer to the reaction mixture includes α,ω-bismethacryloypropyl polydimethylsiloxane.

The reactive mixture may contain additional components such as, but not limited to, UV absorbers, medicinal agents, antimicrobial compounds, reactive tints, pigments, copolymerizable and nonpolymerizable dyes, release agents and combinations thereof. A polymerization catalyst is preferably included in the reaction mixture. The polymerization initiators include compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino) benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitiators which may be used are disclosed in Volume III, Photoinitiators for Free Radical Cationic & Anionic Photopolymerization, $2^{nd}$ Edition by J.V. Crivello & K. Dietliker; edited by G. Bradley; John Wiley and Sons; New York; 1998, which is incorporated herein by reference. The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis (2,6-dimethoxybenzoyl)-2,4-4-trimethylpentyl phosphine oxide (DMBAPO), and the preferred method of polymerization initiation is visible light. The most preferred is bis(2,4,6-trimethylbenzoyl)-phenyl phosphine oxide (Irgacure 8190).

The preferred range of silicone containing monomer present in the reaction mixture is from about 5 to 95 weight percent, more preferably about 30 to 85 weight percent, and most preferably about 45 to 75 weight percent of the reactive components in the reaction mixture. The preferred range of hydrophilic monomer present in the above invention is from about 5 to 80 weight percent, more preferably about 10 to 60 weight percent, and most preferably about 20 to 50 weight percent of the reactive components in the reaction mixture. The preferred range of diluent present in the above invention is from about 2 to 70 weight percent, more preferably about 5 to 50 weight percent, and most preferably about 15 to 40 weight percent of the total reaction mixture (including reactive and nonreactive components). It has been surprisingly found that when the diluents of the present invention are used, wettable biomedical devices, and particularly wettable ophthalmic devices, may be made without incorporating significant quantities of a silicone containing compatibilizing component ("component" may also be referred to herein as "agent").

Preferred combinations of reactive components and diluents are those having from about 25 to about 55 weight % silicone containing monomer, about 20 to about 40 weight % hydrophilic monomer, from about 5 to about 20 weight % of an hydroxyl containing component, from about 0.2 to about 3 weight % of a crosslinking monomer, from about 0 to about 3 weight % of a UV absorbing monomer, from about 2 to about 10 weight % of an high molecular weight hydrophilic polymer (all based upon the weight % of all reactive components) and about 20 to about 50 weight % (weight % of all components, both reactive and non-reactive) of one or more of the claimed diluents.

The reaction mixtures of the present invention can be formed by any of the methods known to those skilled in the art, such as shaking or stirring, and used to form polymeric articles or devices by known methods.

For example, the biomedical devices of the invention may be prepared by mixing reactive components and the diluent(s) with a polymerization initiator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The preferred method for producing contact lenses comprising the polymer of this invention is by the molding of the silicone hydrogels, which is economical, and enables precise control over the final shape of the hydrated lens. For this method, the reaction mixture is placed in a mold having the shape of the final desired silicone hydrogel, i.e., water-swollen polymer, and the reaction mixture is subjected to conditions whereby the monomers polymerize, to thereby produce a polymer/diluent mixture in the shape of the final desired product. Then, this polymer/diluent mixture is treated with a solvent as is known in the art to remove the diluent and ultimately replace it with water, producing a silicone hydrogel having a final size and shape which are quite similar to the size and shape of the original molded polymer/diluent article. This method can be used to form contact lenses and is further described in U.S. Pat. Nos. 4,495,313; 4,680,336; 4,889,664; and 5,039,459, incorporated herein by reference.

The biomedical devices, and particularly ophthalmic lenses of the present invention have a balance of properties which makes them particularly useful. Such properties include clarity, water content, oxygen permeability and contact angle. Thus, in one embodiment, the biomedical devices are contact lenses having a water content of greater than about 17%, preferably greater than about 20% and more preferably greater than about 25%.

As used herein clarity means substantially free from visible haze. Preferably clear lenses have a haze value of less than about 150%, more preferably less than about 100%.

Suitable oxygen permeabilities are preferably greater than about 40 barrer and more preferably greater than about 60 barrer.

Also, the biomedical devices, and particularly ophthalmic devices and contact lenses have contact angles (advancing) which are less than about 80°, preferably less than about 70° and more preferably less than about 65°. In some preferred embodiments the articles of the present invention have combinations of the above described oxygen permeability, water content and contact angle. All combinations of the above ranges are deemed to be within the present invention.

Alpha Values

Alpha values were measured using the following procedure. A 0.05 wt % solution of 4-nitroanisole (Aldrich, CAS#100-17-4) stock solution in HPLC grade methylene chloride was prepared. A 0.1 wt % solution of Dimroth's betaine (Aldrich, CAS #10081-39-7) in HPLC grade methylene chloride was prepared. The stock solution was stored in the dark until used.

To 5 ml of test diluent were added 100 microliters of the above 4-nitroanisole solution to make the 4-nitroanisole test sample solution. The test diluent was placed in the reference beam of the UV-VIS dual beam spectrometer (a Unicam Model UV 300 UV-VIS dual beam spectrometer was used in this procedure). An absorption scan was run from 250 to 350 nm. If maximum absorption was greater than 2 absorbance units, the 4-nitroanisole test sample solution was diluted with test diluent and the absorption scan measurement was repeated. The peak wavelength of the maximum absorption was recorded.

To 5 ml of test diluent were added 500 microliters of the above Dimroth's betaine solution. The test diluent was placed in the reference beam of the UV-VIS dual beam spectrometer. An absorption scan was run from 550 to 800 nm. If maximum absorption was greater than 2 absorbance units, the Dimroth's betaine test sample solution was diluted with test diluent and the absorption scan measurement was repeated. The peak wavelength of the maximum absorption was recorded.

The alpha value was calculated as follows:
1. Convert the $\lambda_{max}$ recorded for the 4-nitroanisole test sample solution in nm to $cm^{-1}$ by inverting and multiplying by $10^7$.
2. Convert the $\lambda_{max}$ recorded for the 4-nitroanisole test sample solution in $cm^{-1}$ to kilokaysers (kK) by dividing by 1000. Designate the result as $\upsilon_1$.
3. Repeat steps 1 and 2 for the $\lambda_{max}$ recorded for the Dimroth dye test sample solution. Designate the result as $\upsilon_{obsd}$.
4. Calculate $\upsilon_{calc} = (-\upsilon \times 1.873) + 74.58$.
5. Calculate $\alpha = (\upsilon_{obsd} - \upsilon_{calc})/6.24$.
   a. The alpha values are shown in Table 1 below.

TABLE 1

| Diluent | P(Mpa$^{-1/2}$) | H (Mpa$^{-1/2}$) | alpha |
|---|---|---|---|
| 1-decanol, >99% | 2.6 | 10.0 | 0.593 |
| 1-dodecanol, >98% | 2.3 | 9.3* | 0.575 |
| 1-octanol, >99% | 3.3 | 11.9 | 0.629 |
| 1-hexanol, >98% | 4.1 | 12.5* | 0.647 |
| 1-pentanol, >99% | 4.5 | 13.9 | 0.685 |
| 2-pentanol | 6.4 | 13.3 | |
| 2-hexanol, >99% | 4.0 | 12.4* | 0.507 |
| 2-octanol | 4.9 | 11.0 | 0.474 |
| 2-decanol | 3.9 | 10.0 | |
| 1-butanol, >99.8% | 5.7 | 15.8 | 0.704 |
| t-amyl alcohol | 4.7 | 13.3* | 0.278 |
| isopropanol, >99.5% | 6.1 | 16.4 | 0.643 |
| 3M3P | 4.1 | 12.5* | 0.211 |
| D3O, >97% | 2.7 | 10.1* | 0.267 |
| ethanol, anhydrous | 8.8 | 19.4 | 0.992 |
| 1-ethoxy-2-propanol, | 8.2 | 13.1 | 0.464 |
| 1-t-butoxy-2-propanol | 6.1 | 12.7* | |
| 2- | 7.4 | 10.5* | 0.378 |
| 2-butanol, >99.5% | 5.7 | 14.5 | 0.540 |
| 1-propanol, >99.5% | 6.8 | 17.4 | 0.743 |
| 2-methyl-2-pentanol, | 4.1 | 12.5* | 0.290 |
| t-butanol, >99% | 5.1 | 14.7 | 0.395 |
| SiGMA acetate | 4.6 | 8.4* | |
| N-ethylacetamide, | 10. | 8.2* | |
| N-tert- | 9* | 7.6* | |
| N- | 10. | 8.3* | |
| N,N- | 14. | 5.5* | |
| N-octylacetamide | 5.6 | 6* | |
| octanoic acid | 3.3 | 8.2 | |
| decanoic acid | 2.3 | 7.7* | |
| lauric (dodecanoic) | 2* | 7.1* | |
| valeric acid | 4.1 | 10.3* | |
| Dimethylsulfoxide | 16. | 10.2 | 0.0* |
| acetonitrile, >99% | 18. | 6.1 | 0.0* |
| N-methylpyrrolidone | 12. | 7.2 | 0.0* |
| Acetone | 10. | 7.0 | 0.08* |
| THF, >99% | 5.7 | 8.0 | 0.0* |
| EtOAc | 5.3 | 7.2 | 0.0* |
| toluene, >99.8% | 1.4 | 2.0 | 0.0* |
| Triethylamine | 0.4 | 1.0 | 0.0* |
| Dodecane | 0.0 | 0.0 | 0.0* |
| methanol, >99.9% | 12. | 22.3 | 0.949 |
| acetic acid, glacial | 8.0 | 13.5 | 1.120 |
| CHCl3, >99.5% | 3.1 | 5.7 | −0.028 |

*Indicated alpha values are from Kamlet, M. J., Abboud, J. M., Abraham, M. H. and Taft, R. W.; J. Org. Chem., 1983, 48, 2877.

Hansen Solubility Parameter

The Hansen solubility parameter, $\delta p$ may be calculated by using the group contribution method described in Barton, CRC Handbook of Solubility Par., 1st. Ed. 1983, page 85-87 and using Tables 13, 14.

Haze Measurement

Haze is measured by placing a hydrated test lens in borate buffered saline in a clear 20×40×10 mm glass cell at ambient temperature above a flat black background, illuminating from below with a fiber optic lamp (Titan Tool Supply Co. fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 1.0 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens. Preferably, lenses have haze levels of less than about 150% (of CSI as set forth above) and more preferably less than about 100%.

Water Content

The water content of contact lenses was measured as follows: Three sets of three lenses are allowed to sit in packing solution for 24 hours. Each lens is blotted with damp wipes and weighed. The lenses are dried at 60° C. for four hours at a pressure of 0.4 inches Hg or less. The dried lenses are weighed. The water content is calculated as follows:

$$\% \text{ water content} = \frac{(\text{wet weight} - \text{dry weight})}{\text{wet weight}} \times 100$$

The average and standard deviation of the water content are calculated for the samples and are reported.

Modulus

Modulus is measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width is loaded into the grips and elongated at a constant rate of strain of 2 in/min. until it breaks. The initial gauge length of the sample (Lo) and sample length at break (Lf) are measured. Twelve specimens of each composition are measured and the average is reported. Percent elongation is =[(Lf−Lo)/Lo]×100. Tensile modulus is measured at the initial linear portion of the stress/strain curve.

Advancing Contact Angle

The advancing contact angle was measured as follows. Four samples from each set were prepared by cutting out a center strip from the lens approximately 5 mm in width and equilibrated in packing solution. The wetting force between the lens surface and borate buffered saline is measured at 23° C. using a Wilhelmy microbalance while the sample is being immersed into or pulled out of the saline. The following equation is used $$F=2\gamma p \cos\theta \text{ or } \theta=\cos^{-1}(F/2\gamma p)$$

where F is the wetting force, γ is the surface tension of the probe liquid, p is the perimeter of the sample at the meniscus and θ is the contact angle. The advancing contact angle is obtained from the portion of the wetting experiment where the sample is being immersed into the packing solution. Each sample was cycled four times and the results were averaged to obtain the advancing contact angles for the lens.

DK

The Dk is measured as follows. Lenses are positioned on a polarographic oxygen sensor consisting of a 4 mm diameter gold cathode and a silver ring anode then covered on the upper side with a mesh support. The lens is exposed to an atmosphere of humidified 2.1% $O_2$. The oxygen that diffuses through the lens is measured by the sensor. Lenses are either stacked on top of each other to increase the thickness or a thicker lens is used. The L/Dk of 4 samples with significantly different thickness values are measured and plotted against the thickness. The inverse of the regressed slope is the Dk of the sample. The reference values are those measured on commercially available contact lenses using this method. Balafilcon A lenses available from Bausch & Lomb give a measurement of approx. 79 barrer. Etafilcon lenses give a measurement of 20 to 25 barrer. (1 barrer=$10^{-10}$ ($cm^3$ of gas×$cm^2$)/($cm^3$ of polymer×sec×cm Hg)).

The Examples below further describe this invention, but do not limit the invention. They are meant only to suggest a method of practicing the invention. Those knowledgeable in the field of contact lenses as well as other specialties may find other methods of practicing the invention. However, those methods are deemed to be within the scope of this invention.

mPDMS-OH mono-(3-methacryloxy-2-hydroxypropyloxy)propyl terminated, mono-butyl terminated polydimethylsiloxane (MW 1100), prepared as in Preparation 1, may be used in the present invention.

Preparation 1

Macromer Prepared as described in US20030052424, Example 1

Zeonor Cyclo olefin thermoplastic polymer from Nippon Zeon Co., Ltd.

A three neck, 500 mL round bottom flask equipped with a magnetic stirrer, reflux condenser w/drying tube, and a thermocouple was charged with 5.0 g (0.054 mole) dry lithium methacrylate. Methacrylic acid (50.0 g, 0.584 mole) and 1.0 g p-methoxyphenol were added to the system, which was stirred while adding 200 g (about 0.20 mole) monoglycidoxypropyl polydimethylsiloxane (1000 $M_N$) to the flask. The reaction mixture was heated to 90° C. The mixture was heated for 15 hours at the given temperature, allowed to cool to ambient conditions, and diluted with 250 mL of ethyl acetate.

The organics were washed two times with 250 mL of 0.5N aqueous sodium hydroxide. Once all the methacrylic acid present in the mixture was neutralized, separation of the two layers dramatically slowed down. The third and fourth washes were performed using an aqueous solution of 0.5N sodium hydroxide and 5% wt/volume sodium chloride in order to speed up the separation process.

The organics were dried over 30 g of anhydrous sodium sulfate, and filtered through a flitted glass funnel containing 75 g of flash grade silica gel to remove any remaining salts in the system. The filtrate was freed of volatile material in a rotary evaporator at 55° C. under a pressure of approximately 10 mbar.

The product, mono-(3-methacryloxy-2-hydroxypropyloxy)propyl terminated, mono-butyl terminated polydimethylsiloxane (MW 1100), was isolated as a colorless, clear liquid, 173.0 g, 79.7%.

Some of the other materials that are employed in the Examples are identified as follows:

TRIS-VC [3-[tris(trimethylsiloxy)silyl]propyl vinyl carbamate] was prepared following the procedure of U.S. Pat. No. 5,070,215, Example 4.5.

$V_2D_{25}$[α-[[4-[[(ethenyloxy)carbonyl]oxy]butyl]dimethylsilyl]-ω-[[[4-[[(ethenyloxy)carbonyl]oxy]butyl]dimethylsilyl]oxy]-Poly[oxy(dimethylsilylene)]] was prepared following the procedure of U.S. Pat. No. 5,070,215, Examples 4.8 and 4.9.

VINAL [N-vinyloxy carbonyl beta-alanine] was prepared following the procedure of U.S. Pat. No. 5,062,995, Examples 1 and 2, and purifying the product by dissolving it in water and extracting it into ethyl acetate, washing the ethyl acetate solution once with water and removing the solvent by rota-evaporation.
DMA N,N-dimethylacrylamide
HEMA 2-hydroxyethyl methacrylate
mPDMS 800-1000 MW ($M_n$) monomethacryloxypropyl terminated mono-n-butyl terminated polydimethylsiloxane
Norbloc 2-(2'-hydroxy-5-methacrylyloxyethylphenyl)-2H-benzotriazole
PVP poly(N-vinyl pyrrolidone) (K value 90)
SiGMA acetate acetic acid, 2-hydroxy-3-[3-[1,3,3,3-tetramethyl-1-[(trimethylsilyl)oxy]disiloxanyl]propoxy] propyl ester
SIGMA diol 2,3-dihydroxypropyloxypropyl-bis(trimethylsiloxy)-methylsilane
IPA isopropyl alcohol
D3O 3,7-dimethyl-3-octanol
3M3P 3-methyl-3-pentanol
2M2P 2-methyl-2-pentanol
TEGDMA tetraethyleneglycol dimethacrylate
TRIS 3-methacryloxypropyltris(trimethylsiloxy)silane
CGI 819 bis(2,4,6-trimethylbenzoyl)-phenyl phosphine oxide
CGI1850 1:1 (wgt) blend of 1-hydroxycyclohexyl phenyl ketone and bis(2,6-dimethoxybenzoyl)-2,4-4-trimethyl-pentyl phosphine oxide
NVP N-vinylpyrrolidone
MAA methacrylic acid

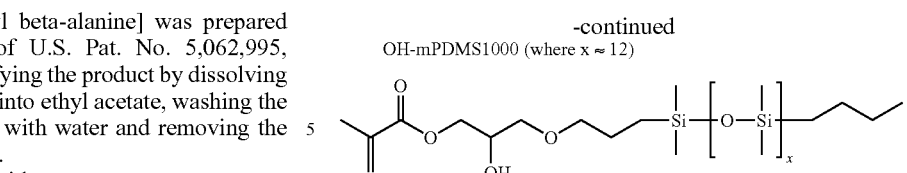

OH-mPDMS1000 (where x ≈ 12)

Example 1

The compounds listed in Table 2 below were screened for compatibility with mPDMS, DMA and PVP (K90) using the following procedure: mPDMS was added dropwise to a pre-weighed vial of a rapidly stirring solution of 1.67 g DMA, 0.33 g PVP and 2.0 g of the test diluent at room temperature until the resulting mix becomes hazy and does not become clear after stirring for several minutes. The mass of added mPDMS is determined and reported in Table 2.

The diluents were purchased from sources as follows:
Aldrich Chemicals: 1-decanol, 1-dodecanol, 1-octanol, 1-pentanol, 1-hexanol, decanoic acid, 2-hexanol, 2-octanol, 2-pentanol, 1-butanol, t-amyl alcohol, isopropanol, 2-(diisopropylamino)ethanol, tetrahydrofuran, acetone, diethylcarbonate, ethyl acetate, valeric acid, dipropyleneglycol methyl ether acetate, N,N-dimethylpropionamide, acetonitrile, 2-methyl-2,4-pentanediol, N-t-butylformamide, ethyl (S) lactate, N-ethylacetamide, solketal, N-methylpropionamide, dimethylsulfoxide, dodecane, isopropyl acetate, N-ethyl-2-methallylamine, and triethylamine.

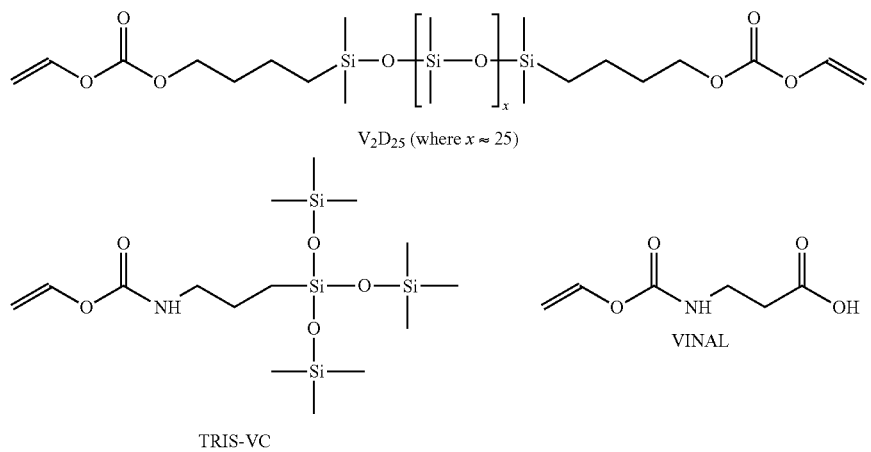

$V_2D_{25}$ (where x ≈ 25)

TRIS-VC

VINAL acPDMS 2000 bis-3-acryloxy-2-hydrorxypropyloxypropyl polydimethylsiloxane, (Molecular weight is ~2000) commercially available from Goldschmidt Chemical Corporation under the name Tegomer V-S 2250

SiMAA

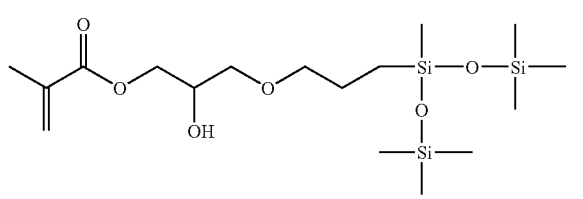

Fluka: 3-methyl-3-pentanol, ethanol, chloroform and toluene.
Millennium Chemicals: D3O.
Fisher Scientific: methanol and acetic acid.
Acros: 1-ethoxy-2-propanol.
Gelest: 3-aminopropyltris(trimethylsiloxy) silane, tetraethoxysilane, mPDMS 1000, octamethylcyclotetrasiloxane and DMS-C15.
Jarchem: DMA. PVP K90 was purchased from ISP.
N-octylacetamide was prepared by reacting acetic anhydride with 1-octylamine in methanol at room temperature in the presence of $Na_2CO_3$ and was characterized by FTIR.

SiGMA acetate was prepared by reacting (3-glycidoxypropyl)bis(trimethylsiloxy)methylsilane with acetic acid, catalyzed by lithium acetate and was characterized by GC/MS. SiGMA diol was prepared by platinum catalyzed hydrosilylation of 2,3-dihyroxypropyl allyl ether with 1,1,1,3,5,5,5 hexamethyltrisiloxane and was characterized by GC/MS, FTIR and NMR. The minimum purities of test diluents, where known, are shown in Table 1.

TABLE 2

| Diluent | g mPDMS* | functional group |
|---|---|---|
| 1-decanol, 99% | 2.95 | alcohol (1) |
| 1-dodecanol, 98% | 2.86 | alcohol (1) |
| 1-octanol, 99% | 2.83 | alcohol (1) |
| 1-hexanol, 98% | 2.57 | alcohol (1) |
| 1-pentanol, >99% | 2.30 | alcohol (1) |
| decanoic acid, >99% | 2.28 | carboxylic acid |
| 2-octanol, 97% | 2.23 | alcohol (2) |
| 2-pentanol, 98% | 2.14 | alcohol (2) |
| 1-butanol, 99.8% | 2.17 | alcohol (1) |
| t-amyl alcohol, 99% | 2.02 | alcohol (3) |
| Isopropanol, 99.5% | 1.85 | alcohol (2) |
| 3-methyl-3-pentanol, >98% | 1.80 | alcohol (3) |
| D3O, >97% | 1.72 | alcohol (3) |
| ethanol, anhydrous | 1.22 | alcohol (1) |
| SiGMA diol | 1.14 | alcohol (1 & 2) |
| 1-tert-butoxy-2-propanol, >98% | 1.04 | alcohol (2) & ether |
| 2-(diisopropylamino)ethanol, 99% | 1.02 | alcohol (1) & amine |
| SiGMA acetate | 1.00 | alcohol (2) and ester |
| 1-ethoxy-2-propanol, 90-95% | 0.67 | alcohol (2) & ether |
| Chloroform, >99.5% | 0.57 | alkyl halide |
| Tetrahydrofuran, 99.9% | 0.33 | Ether |
| N-octylacetamide | 0.33 | Amide |
| toluene, 99% | 0.33 | Aromatic |
| acetone, 99.5% | 0.27 | Ketone |
| Diethylcarbonate, 99% | 0.19 | Carbonate |
| ethyl acetate, 99.5% | 0.19 | Ester |
| Valeric acid, 99% | 0.18 | carboxylic acid |
| methanol, >99.9% | 0.17 | alcohol (1) |
| Dipropyleneglycol methyl ether acetate, >99% | 0.15 | ether, ester |
| N,N-dimethylpropionamide | 0.15 | Amide |
| Acetonitrile, >99% | 0.14 | Nitrile |
| 2-methyl-2,4-pentanediol | 0.12 | alcohol (2 & 3) |
| N-t-butylformamide, 98% | 0.12 | Amide |
| Acetic acid, glacial | 0.08 | Acid |
| ethyl (S) lactate, 98% | 0.06 | alcohol (2) & ester |
| N-ethylacetamide, 99% | 0.06 | Amide |
| 2-(methoxyethoxy)ethanol | 0.05 | alcohol (1) & ether |
| N-methylpyrrolidone | 0.05 | Amide |
| Solketal | 0.05 | alcohol (1) and ether |
| N-methylpropionamide, 98% | 0.05 | Amide |
| Water | 0.03 | |
| Dimethylsulfoxide, 99.9% | 0.01 | Sulfoxide |
| 3-aminopropyltris-(trimethylsiloxy)silane | 0.00 | amine & siloxane |
| Octamethylcyclotetrasiloxane | 0.00 | Siloxane |
| Dodecane | 0.00 | Alkane |
| DMS-C15 PDMS-PEG carbinol (Gelest) | 0.00 | alcohol, PEG, siloxane |
| isopropyl acetate, 99% | 0.00 | Ester |
| N-ethyl-2-methallylamine, 98% | 0.00 | amine, olefin |
| Tetraethoxysilane | 0.00 | Alkoxysilane |
| Triethylamine | 0.00 | Amine |

*0.00 g indicates that the blend was inhomogenous before addition of any mPDMS.

Diluents which are capable of forming a clear blend with about 0.6 or more grams of mPDMS in the above mixtures display desirable preliminary compatibility with the test components.

Examples 2-23

Some of the diluents from Example 1 were used to make contact lenses from the monomer mix shown in Table 3.

TABLE 3

| Component | level (wt) |
|---|---|
| DMA | 31% |
| PVP (K90) | 6% |
| mPDMS 1000 | 45% |
| HEMA | 14.75% |
| CGI-819 | 0.25% |
| TEGDMA | 1.5% |
| Norbloc | 1.5% |
| monomer/diluent ratio | 60/40 |

HEMA was purchased from Rohm. CGI-819 and CGI 1850 were purchased from CIBA Specialty Chemicals. TEGDMA was purchased from Esstech and Norbloc was purchased from Janssen.

The components were combined and mixed overnight at room temperature.

The monomer mix (75 microliter per cavity) was dispensed in a nitrogen glove box, into front curves made from Topas® copolymers of ethylene and norbornene obtained from Ticona Polymers. Polypropylene back curves were mated to the front curves, closing the mold. Lenses were cured by irradiating with Philips TL 20 W/03T fluorescent bulbs at 45° C. for about 30 minutes in $N_2$. The molds were opened and lenses were extracted into 70/30 (vol/vol) $IPA/H_2O$, washed with two fresh exchanges of this solution, and then placed into deionized water and observed for clarity. The results are shown in Table 4.

TABLE 4

| Ex# | Diluent | Blend clarity | Lens haze (%) |
|---|---|---|---|
| 2 | D3O | Clear | 18 |
| 3 | 1-decanol | Clear | 26 |
| 4 | 1-octanol | Clear | 29 |
| 5 | 1-pentanol | Clear | 33 |
| 6 | 1-hexanol | Clear | 31 |
| 7 | 2-hexanol | Clear | 50 |
| 8 | 2-octanol | Clear | 46 |
| 9 | 1-dodecanol | Clear | 32 |
| 10 | 3-methyl-3-pentanol | Clear | 16 |
| 11 | t-amyl alcohol | Clear | 13 |
| 12 | t-butanol | Clear | 13 |
| 13 | 2-butanol | Clear | 58 |
| 14 | 1-butanol | Clear | 31 |
| 15 | 2-methyl-2-pentanol | Clear | 13 |
| 16 | 2-propanol | Clear | 29* |
| 17 | 1-propanol | Clear | 49 |
| 18 | Ethanol | Clear | 64* |
| 19 | 2-ethyl-1-butanol | Clear | 22 |
| 20 | SiGMA acetate | Clear | Opaque |
| 21 | Decanoic acid | Clear | Opaque |
| 22 | 1-t-butoxy-2-propanol | Opaque | — |
| 23 | 1-ethoxy-2-propanol | Opaque | — |

*Lenses were misshapen

The mechanical properties of lenses from examples 5, 6 and 14 were measured and are reported in Table 5. The results show that, in three isomeric hexanols, the modulus of the lenses made with a secondary alcohol is reduced as compared to those made with primary or tertiary alcohols. While not wishing to be bound by theory, it is believed that hydrogen atom abstraction from secondary alcohol diluents may effect cure in a manner that may reduce the modulus as well as the clarity (see Table 4) of the resulting lenses.

TABLE 5

| Ex# | Alcohol type | Diluent | Modulus (psi) | Elongation (%) |
|---|---|---|---|---|
| 6 | Primary | 1-hexanol | 75 ± 7 | 251 ± 72 |
| 7 | Secondary | 2-hexanol | 64 ± 4 | 200 ± 71 |
| 15 | Tertiary | 2-methyl-2-pentanol | 77 ± 8 | 209 ± 104 |

Examples 24

Lenses were made from the components shown in Table 6, below in grams. The components were mixed overnight at room temperature to give a clear blend. The reactive mixture was charged in a nitrogen box, into lens molds comprising front curves made from Topas® copolymers of ethylene and norbornene obtained from Ticona Polymers and polypropylene back curves. Lenses were cured with 1.3 mW/cm$^2$ from Philips TL 20 W/03T fluorescent bulbs at 60° C. for about 30 minutes in $N_2$. The molds were opened and lenses were extracted into IPA, and soaked in IPA at ambient temperature for about one hour to remove residual diluent and monomers, stepped down into an approximately 50:50 solution of IPA and water, and then placed into deionized water and observed for clarity. The lenses were optically clear, soft and wettable. Lens properties are shown in Table 8, below.

Tables 6, 7, 9, 10 and 11 list the components by weight % as follows. Components except the diluent are given in weight % of the composition absent the diluent. The diluent is given in a weight % of the composition including the diluent.

TABLE 6

| MPDMS | 46 |
|---|---|
| DMA | 35 |
| HEMA | 9.5 |
| TEGDMA | 1.5 |
| PVP K90 | 7 |
| CGI 1850 | 1 |
| Diluent | D3O |
| Diluent % | 36.0 |

Example 25

Lenses were made from the components shown in Table 7, below in grams. The components were mixed overnight at room temperature to give a clear blend.

TABLE 7

| MPDMS | 45.0 |
|---|---|
| DMA | 31.0 |
| HEMA | 15.25 |
| EGDMA | 1.0 |
| Norbloc | 1.5 |
| PVP K90 | 6.0 |
| CGI 819 | 0.25 |
| Diluent | t-amyl alcohol |
| Diluent % | 40.0 |
| Cure Temp. | 60-65° C. |

The reactive mixture was charged to a lens mold comprising front curves made from Topas® copolymers of ethylene and norbornene obtained from Ticona Polymers in a nitrogen box, and with polypropylene back curves. Lenses were cured irradiating with 1.3 mW/cm$^2$ from Philips TL 20 W/03T fluorescent bulbs at the temperature indicated for about 15 minutes in $N_2$. The molds were opened and lenses were extracted into a 70/30 blend (v/v) of IPA/water, changing this mixture twice with fresh 70/30 IPA/water, and then placed into deionized water. The results are shown in Table 8.

TABLE 8

| Property | Ex. 24 | Ex. 25 |
|---|---|---|
| % EWC | 56.2 ± 0.2 | 43.7 ± 0.3 |
| Dk (barrers) | 71 | 63 |
| Modulus (psi) | 60 ± 5.9 | 118.4 ± 7.3 |
| Elongation (%) | 144 ± 42 | 155 ± 47 |
| DCA | 63 ± 7 | 46 ± 14 |
| Clarity | Clear | 8 ± 1 |

Examples 26-27

Fluoroether-siloxane-methacrylate macromer was prepared following the procedure of Example B-5 in U.S. Pat. No. 5,760,100. The blend shown in Table 9 was prepared by combining the listed components and mixing overnight at room temperature. Lenses were made by filling TOPAS mold front curves in a nitrogen atmosphere with 75 microliters of the monomer mix, closing the molds with a polypropylene beck curve and irradiating for 30 minutes with Philips TL 20 W/09N fluorescent bulbs at room temperature. The molds were separated and the lenses were released into a solution of 70/30 (v/v) IPA and water. The lenses were leached in this solution with two exchanges for fresh solution, leaching at least 30 minutes per cycle, then placed into borate-buffered saline solution. The advancing DCA (dynamic contact angle) of the lenses was determined and the results are shown in Table 9, below.

Example 26 was repeated except that PVP and HEMA were added, and the amount of the TRIS and DMA decreased to allow for the additional components. The amounts of the components are shown in Table 9, below. Lenses were made according to Example 26, the advancing DCA was determined and the results are shown in Table 9, below.

TABLE 9

|  | Example 26 | Example 27 |
|---|---|---|
| Macromer | 50 | 50 |
| TRIS | 20 | 25 |
| DMA | 30 | 17 |
| PVP (K 90) | 0 | 3 |
| HEMA | 0 | 5 |
| Darocur 1173 | 0.58 | 0.58 |
| Diluent | 22 (ethanol) | 67 (D3O) |
| Blend | Clear | Clear |
| Lens | clear and flexible | clear and flexible |
| Advancing DCA | 128 ± 10° | 57 ± 12° |

Thus, by proper diluent selection, hydrogels comprising silicone containing monomers may be formed into wettable, ophthalmic devices, without any surface treatment process.

Other examples follow, which use PVP as internal wetting agents.

Example A: Lenses were made by filling TOPAS mold front curves in a nitrogen atmosphere with monomer mix, closing the molds with a polypropylene back curve and irradiating for 40 minutes with Philips TL 20 W/09N fluorescent bulbs at room temperature. The molds were separated and the lenses were released into a solution of 70/30 (v/v) IPA and water. The lenses were then transferred into deionized water, and then placed into borate-buffered saline solution.

Examples B and C: Lenses were made by filling TOPAS mold front curves in a nitrogen atmosphere with monomer mix, closing the molds with a polypropylene back curve and irradiating for 30 minutes with Philips TL 20 W/09N fluorescent bulbs at room temperature. The molds were separated and the lenses were released into a solution of 70/30 (v/v) IPA and water. The lenses were leached in this solution with two exchanges of fresh solution, and then placed into borate-buffered saline solution.

Examples D, E and F: Lenses were made by filling TOPAS mold front curves in a nitrogen atmosphere with monomer mix, closing the molds with a polypropylene back curve and irradiating for 40 minutes with Philips TL 20 W/09N fluorescent bulbs at 55° C. The molds were separated and the lenses were released into a solution of 70/30 (v/v) IPA and water. The lenses were leached in this solution with two exchanges of fresh solution, and then stepped down into 50/50 (v/v) IPA and water, followed by 30/70 (v/v) IPA and water, and then into water, allowing ~30 minutes per cycle. Finally, the lenses were placed into borate-buffered saline solution.

Example B': Lenses were made by filling TOPAS mold front curves in a nitrogen atmosphere with monomer mix, closing the molds with a polypropylene back curve and irradiating for 30 minutes with Philips TL 20 W/09N fluorescent bulbs at room temperature (~23° C.). The molds were separated and the lenses were released into a solution of 70/30 (v/v) IPA and water. The lenses were leached in this solution with three exchanges of fresh solution, and then stepped down into 50/50 (v/v) IPA and water, followed by 30/70 (v/v) IPA and water, and then into water, allowing ~30 minutes per cycle. Finally, the lenses were placed into borate-buffered saline solution.

TABLE 11

| Component | Example D | Example F |
|---|---|---|
| ac PDMS2000 | 16 | 16 |
| SiMAA | 26 | 26 |
| MPDMS OH-1000 | 30 | 30 |
| MAA | 0.5 | 0.5 |
| DMA | 24.25 | 19.25 |
| PVP (K90) | 4 | 4 |
| HEMA | 0 | 5 |
| DAROCUR 1173 | 0.5 | 0.5 |
| DILUENT Type | D3O | D3O |
| DILUENT | 33 | 33 |
| Blend | Clear | Clear |
| Wettability | Not Wettable* | Wettable |
| Lens Clarity | Hazy/Opaque | Clear |

*Advancing contact angle >80°.

Example F had an advancing contact angle of 65+/−9°, Dk (barrers) of 160, Modulus (psi) of 230+/−11, and Haze of 6+/−1.

It is understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A composition comprising:
at least one silicone containing component,
at least one hydrophilic component,

TABLE 10

Comparative formulations

| Component | Example B' | Example B | Example A | Example C | Example E |
|---|---|---|---|---|---|
| $V_2D_{25}$ | 15 | 15 | 15 | 15 | 15 |
| TRIS-VC | 54 | 55 | 50 | 50 | 55 |
| VINAL | 1 | 1 | 1 | 1 | 1 |
| NVP | 30 | 30 | 18 | 24 | 26 |
| PVP (K90) | 0 | 0 | 6 | 0 | 4 |
| HEMA | 0 | 0 | 10 | 10 | 0 |
| DAROCUR 1173 | 0.2 | 0.35 | 0.35 | 0.35 | 0.35 |
| DILUENT | 13 | 15 | 40 | 20 | 60 |
| DILUENT Type | n-nonanol | D3O | D3O | D3O | D3O |
| Blend | Clear | Clear | Clear | Clear | Clear |
| Wettability | Not Wettable*** | Not Wettable*** | Not Wettable*** | Not Wettable*** | Not Wettable*** |
| Lens Clarity | Clear* | Clear* | Hazy/Opaque** | Hazy/Opaque** | Hazy/Opaque** |

*Clear is < about 100% v. CSI
**Hazy/opaque is haze > about 200% v. CSI
***Advancing contact angle >80°
"D3O" means 3,7-dimethyl-3-octanol.

Example B' had an Advancing Contact Angle of 97+/−5° and Haze of 18+/−3.

As is apparent in examples A, B, C and E, it is believed, without being limited to mechanism, that the significant differences in polymerization kinetics of HEMA and the other monomers caused at least some of the resultant haze in lenses.

In example F, it is believed, without being limited to mechanism, clear and wettable lenses resulted from HEMA making PVP more compatible as the internal wetting agent and similar polymerization kinetics among the monomers used.

at least one high molecular weight hydrophilic polymer, and at least one diluent having an alpha value of between about 0.05 and about 1 and a Hansen solubility parameter, δp, of less than about 10, wherein the composition forms a clear blend at a selected reaction temperature, wherein the reaction temperature is up to about 75C., and wherein the composition further comprises at least one silicone containing compatibilizing component in an amount insufficient to compatibilize the blend absent the diluent.

2. The composition of claim 1 wherein the alpha value is between about 0.1 and about 0.9.

3. The composition of claim 1 wherein the hydrophilic component and the silicone containing component are polymerizable and the composition forms a clear article when polymerized at the reaction temperature.

4. The composition of claim 1 wherein the diluent is selected from the group consisting of alcohols having at least three carbon atoms.

5. The composition of claim 1 wherein the diluent is selected from the group consisting of alcohols having at least four carbon atoms.

6. The composition of claim 1 wherein the diluent is selected from the group consisting of alcohols having at least six carbon atoms.

7. The composition of claim 1 wherein the δp of less than about 6.

8. The composition of claim 1 wherein the silicone containing compatibilizing component is present in an amount between about 0 and about 5 weight % of the composition.

9. The composition of claim 1 wherein diluent is one or more selected from the group consisting of 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, SiGMA acetate, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino)ethanol and mixtures thereof.

10. The composition of claim 1 wherein the diluent is one or more selected from the group consisting of 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid and mixtures thereof.

11. The composition of claim 1 wherein the diluent is one or more selected from the group consisting of 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol and mixtures thereof.

12. The composition of claim 1 wherein the high molecular weight hydrophilic polymer has a molecular weight greater than about 150,000 Daltons.

13. The composition of claim 1 wherein the high molecular weight hydrophilic polymer has a molecular weight between about 150,000 to about 2,000,000 Daltons.

14. The composition of claim 1 wherein the high molecular weight hydrophilic polymer has a molecular weight between about 500,000 to about 1,500,000 Daltons.

15. The composition of claim 1 wherein the high molecular weight hydrophilic polymer is present in an amount between about 1 to about 15 weight % of the composition.

16. The composition of claim 1 wherein the high molecular weight hydrophilic polymer is present in an amount between about 3 to about 12 weight % of the composition.

17. The composition of claim 1 wherein the high molecular weight hydrophilic polymer comprises a cyclic amide in a backbone of the high molecular weight hydrophilic polymer.

18. The composition of claim 1 wherein the high molecular weight hydrophilic polymer comprises a cyclic imide in a backbone of the high molecular weight hydrophilic polymer.

19. The composition of claim 1 wherein the high molecular weight hydrophilic polymers is one or more selected from the group consisting of poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N-N-dimethylacrylamide, polyvinyl alcohol, polyacrylic acid, polyethylene oxide, poly 2 ethyl oxazoline, heparin polysaccharides, polysaccharides, and mixtures, block copolymers, random copolymers, branched copolymers, multichain copolymers, comb-shaped copolymers, and star shaped copolymers thereof.

20. The composition of claim 1 wherein the high molecular weight hydrophilic polymer comprises poly-N-vinylpyrrolidone.

21. The composition of claim 1 wherein the reaction temperature is about 40° C.

22. The composition of claim 1 wherein at least one component comprises a least one hydrogen bond donor group and at least one component comprises at least one hydrogen bond acceptor group and said composition comprises a ratio of moles hydrogen bond donor groups to moles of hydrogen bond acceptor groups in said high molecular weight hydrophilic polymer is ≧about 0.8 for the composition.

23. The composition of claim 1 wherein at least one component comprises a least one hydrogen bond donor group, said silicone containing component comprises silicon and said composition comprises a ratio of moles of hydrogen bond donor group to moles of silicon greater than about 0.14 for the composition.

24. A composition comprising
at least one silicone containing component,
at least one hydroxyl containing component,
at least one high molecular weight hydrophilic polymer, and
at least one diluent having an alpha value of between about 0.05 and about 1 and a Hansen solubility parameter, δp, of less than about 10, wherein the composition forms a clear blend at a selected reaction temperature, wherein the reaction temperature is up to about 75° C., wherein the composition further comprises at least one silicone containing compatibilizing component in an amount insufficient to compatibilize the blend absent the diluent.

25. The composition of claim 24 wherein the hydroxyl containing component comprises at least one polymerizable double bond and at least one hydrophilic functional group.

26. The composition of claim 25 wherein the polymerizable double bond is one or more selected from the group consisting of acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds.

27. The composition of claim 24 wherein the hydroxyl containing component is one or more selected from the group consisting of 2-hydroxyethyl methacrylate, 2-hydroxyethyl acrylate, 2-hydroxyethyl methacrylamide, 2-hydroxyethyl acrylamide, 2-hydroxyethyl vinyl carbamate, 2-hydroxyethyl vinyl carbonate, 2-hydroxypropyl methacrylate, hydroxyhexyl methacrylate, hydroxyoctyl methacrylate and mixtures thereof.

28. The composition of claim 24 wherein the hydroxyl containing component comprises 2-hydroxyethyl methacrylate.

29. The composition of claim 24 wherein the silicone containing component comprises a fluoroether-siloxane-methacrylate macromer.

30. The composition of claim 25 or 29 wherein the hydroxyl containing component comprises 2-hydroxyethyl methacrylate and
the high molecular weight hydrophilic polymer comprises poly-N-vinylpyrrolidone.

31. The composition of claim 25 wherein the silicone containing component comprises monomethacryloxypropyl terminated mono-n-butyl terminated polydimethylsiloxane.

32. The composition of claim 31 wherein the hydroxyl containing component comprises 2-hydroxyethyl methacrylate and
the high molecular weight hydrophilic polymer comprises poly-N-vinylpyrrolidone.

33. The composition of claim 24 wherein the reaction temperature is about 40° C.

34. A composition comprising
about 1 part by weight of at least one silicone containing component,
about 1.6 parts by weight of at least one hydrophilic component,
about 0.3 parts by weight of at least one high molecular weight hydrophilic polymer and
about 2 parts by weight diluent, and the composition is a compatible mixture at about room temperature.

35. The composition of claim 34 wherein the hydrophilic component comprises
DMA,
the silicone containing component comprises monomethacryloxypropyl terminated mono-n-butyl terminated polydimethylsiloxane, and
the high molecular weight hydrophilic polymer comprises PVP.

36. An ophthalmic device comprising a cured compound, wherein the compound in precure form comprises
at least one silicone containing component,
at least one hydrophilic component,
at least one high molecular weight hydrophilic polymer, and
at least one diluent having an alpha value of between about 0.05 and about 1 and a Hansen solubility parameter, $\delta p$, of less than about 10, wherein the procure form further comprises at least one silicone containing compatibilizing component in an amount insufficient to compatibilize the blend absent the diluent.

37. An ophthalmic device comprising a cured compound, wherein the compound in precure form comprises
at least one silicone containing component,
at least one hydroxyl containing component,
at least high molecular weight hydrophilic polymer, and
at least one diluent having an alpha value of between about 0.05 and about 1 and a Hansen solubility parameter, $\delta p$, of less than about 10, wherein the procure form further comprises at least one silicone containing compatibilizing component in an amount insufficient to compatibilize the blend absent the diluent.

38. A method of making a clear and wettable ophthalmic device comprising
Forming a reaction mixture comprising at least one silicone containing component, at least one hydrophilic component, at least one high molecular weight hydrophilic polymer, at least one diluent having an alpha value of between about 0.05 and about 1 and a Hansen solubility parameter, $\delta p$, of less than about 10 and at least one silicone containing compatibilizing component in an amount insufficient to compatibilize the reaction mixture absent the diluent,
Placing the reaction mixture in a mold,
Curing the reaction mixture to form the ophthalmic device,
Releasing the ophthalmic device from the mold, and
Removing substantially all of the diluent from the ophthalmic device.

39. A method of making a clear and wettable ophthalmic device comprising
Forming a reaction mixture comprising at least one silicone containing component, at least one hydroxyl containing component, at least one high molecular weight hydrophilic polymer, at least one diluent having an alpha value of between about 0.05 and about 1 and a Hansen solubility parameter, $\delta p$, of less than about 10, and at least one silicone containing compatibilizing component in an amount insufficient to compatibilize the reaction mixture absent the diluent,
Placing the reaction mixture in a mold,
Curing the reaction mixture to form the ophthalmic device, and
Releasing the ophthalmic device from the mold.

40. A composition comprising
monomethacryloxypropyl terminated mono-n-butyl terminated polydimethylsiloxane;
N,N-dimethylacrylamide;
2-hydroxyethyl methacrylate;
tetraethyleneglycol dimethacrylate;
poly(N-vinyl pyrrolidone) (K value 90);
bis(2,4,6-trimethylbenzoyl)-phenyl phosphine oxide; and
3,7-dimethyl-3-octanol.

41. A composition comprising:
monomethacryloxypropyl terminated mono-n-butyl terminated polydimethylsiloxane;
N,N-dimethylacrylamide;
2-hydroxyethyl methacrylate;
ethylene glycol dimethacrylate;
2-(2'-hydroxy-5-methacrylyloxyethylphenyl)-2H-benzotriazole;
poly(N-vinyl pyrrolidone) (K value 90);
bis(2,4,6-trimethylbenzoyl)-phenyl phosphine oxide; and
t-amyl alcohol.

* * * * *

UNITED STATES PATENT AND TRADEMARK OFFICE
CERTIFICATE OF CORRECTION

PATENT NO.         : 8,158,695 B2                                Page 1 of 1
APPLICATION NO.    : 10/794399
DATED              : April 17, 2012
INVENTOR(S)        : Douglas G. Vanderlaan It is certified that error appears in the above-identified patent and that said Letters Patent is hereby corrected as shown below:

In Claim 22, Column 28, line 27 please replace:

philic polymer is $\geqq$ about 0.8 for the composition.

With:

philic polymer is $\geq$ about 0.8 for the composition.

Signed and Sealed this
Third Day of July, 2012

David J. Kappos
*Director of the United States Patent and Trademark Office*